(12) United States Patent
Klopotek

(10) Patent No.: US 6,626,924 B1
(45) Date of Patent: Sep. 30, 2003

(54) SURGICAL MICROTOMES

(75) Inventor: Peter J. Klopotek, 2 Bayberry La., Framingham, MA (US) 01701

(73) Assignee: Peter J. Klopotek, Framingham, MA (US)

( * ) Notice: Subject to any disclaimer, the term of this patent is extended or adjusted under 35 U.S.C. 154(b) by 0 days.

(21) Appl. No.: 09/623,358
(22) PCT Filed: Jun. 1, 1998
(86) PCT No.: PCT/US98/11211
§ 371 (c)(1), (2), (4) Date: Aug. 30, 2000
(87) PCT Pub. No.: WO98/53774
PCT Pub. Date: Dec. 3, 1998

(51) Int. Cl.$^7$ .................................................. A61F 9/00
(52) U.S. Cl. ....................................................... 606/166
(58) Field of Search ................................ 606/166, 167, 606/169, 115, 170, 171, 174

(56) References Cited

U.S. PATENT DOCUMENTS

| 4,298,004 A | 11/1981 | Schachar et al. ............ 128/305 |
| 4,534,348 A | 8/1985 | Fedorov et al. ............. 128/305 |
| 4,660,556 A | 4/1987 | Swinger et al. ............. 128/305 |

(List continued on next page.)

FOREIGN PATENT DOCUMENTS

| DE | 4012882 | 10/1991 |
| EP | 0208950 | 1/1987 |
| EP | 0771553 | 5/1997 |
| WO | 9001905 | 3/1990 |
| WO | 9720529 | 6/1997 |

*Primary Examiner*—Kevin T. Truong
(74) *Attorney, Agent, or Firm*—Thomas J. Engellenner; Nutter McClennen & Fish LLP

(57) ABSTRACT

Methods and apparatus are diclosed for removal of biological tissue slices or layers, preferably in the form of lamellar sections (4) of predetermined shape and thickness employing a reference member (12) that engages a target tissue site and cooperates with a cutter (14) in order to remove the tissue segment or lamella. The cutter can include a flexible cutting element such as a wire or band element that is brought into physical contact with a guiding edge (8) integrated with, or otherwise coupled to, the reference member. Alternatively, the cutter can include a stiff rigid blade element (14B) that is maintained in contact with the guiding edge. The cutter is drawn along a path defined by the guide edge through the tissue to sever, at least partialy, a tissue section. In one particularly useful aspect of the invention, devices for keratectomy are diclosed employing an ocular reference member that engages the upper central region of the cornea and cooperates with a cutter to remove a lamellar segment from the cornea. Such lamellar resections are useful in preparing the cornea for further surgery (by mechanical or laser surgical techniques), or in performing refractive keratectomy directly upon the eye, or in treating (e.g., smoothing) the corneal surface to correct abnormalities, (e.g., to remove ulcerated tissue or otherwise improve the optical properties of the cornea).

35 Claims, 11 Drawing Sheets

U.S. PATENT DOCUMENTS

| | | | |
|---|---|---|---|
| 4,662,370 A | 5/1987 | Hoffmann et al. | 128/305 |
| 4,674,503 A | 6/1987 | Peyman et al. | 128/305 |
| 4,724,837 A | 2/1988 | Gannon | 606/166 |
| 4,763,651 A | 8/1988 | Kaufman et al. | 606/166 |
| 4,840,175 A | 6/1989 | Peyman | 128/303.1 |
| 4,903,695 A | 2/1990 | Warner et al. | 606/4 |
| 5,063,942 A | 11/1991 | Kilmer et al. | 128/898 |
| 5,108,412 A | 4/1992 | Krumeich et al. | 606/166 |
| 5,133,726 A | 7/1992 | Ruiz et al. | 606/166 |
| 5,171,254 A | 12/1992 | Sher | 606/166 |
| 5,188,125 A | 2/1993 | Kilmer et al. | 128/898 |
| 5,215,104 A | 6/1993 | Steinert | 128/898 |
| 5,288,292 A | 2/1994 | Giraud et al. | 606/166 |
| 5,290,301 A | 3/1994 | Lieberman | 606/166 |
| 5,306,282 A | 4/1994 | Muller | 606/169 |
| 5,312,330 A | 5/1994 | Klopotek | 604/49 |
| 5,312,424 A | 5/1994 | Kilmer et al. | 606/151 |
| 5,314,439 A | 5/1994 | Sugita | 606/166 |
| 5,318,044 A | 6/1994 | Kilmer et al. | 128/898 |
| 5,318,046 A | 6/1994 | Rozakis | 128/898 |
| 5,342,378 A | 8/1994 | Giraud et al. | 606/166 |
| 5,368,604 A | 11/1994 | Kilmer et al. | 606/166 |
| 5,395,385 A | 3/1995 | Kilmer et al. | 606/166 |
| 5,496,339 A | 3/1996 | Koepnick | 606/166 |
| 5,556,406 A | 9/1996 | Gordon et al. | 606/166 |
| 5,632,757 A | 5/1997 | Arnott | 606/166 |
| 5,779,723 A | 7/1998 | Schwind | 606/166 |

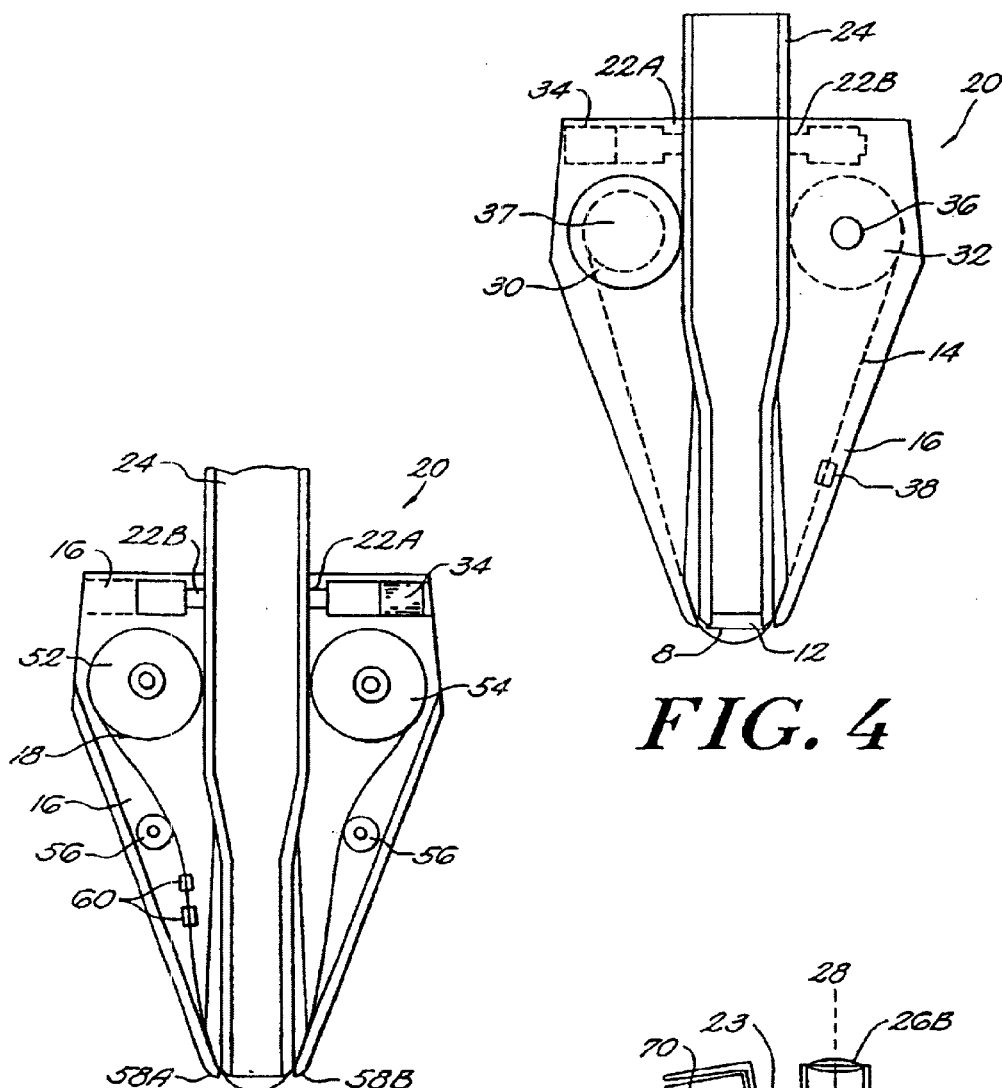
FIG. 4
FIG. 5
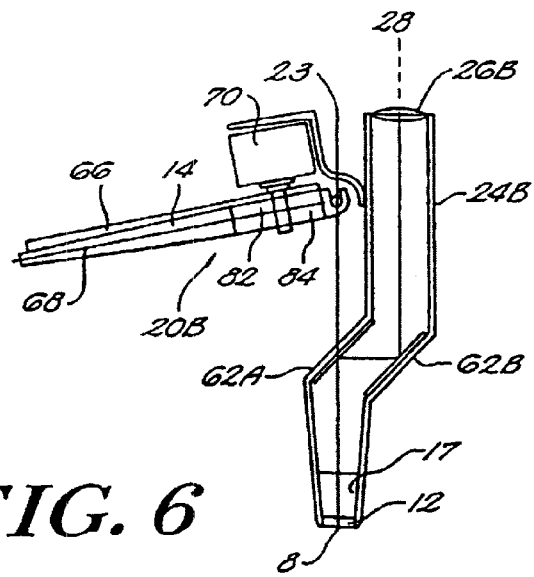
FIG. 6

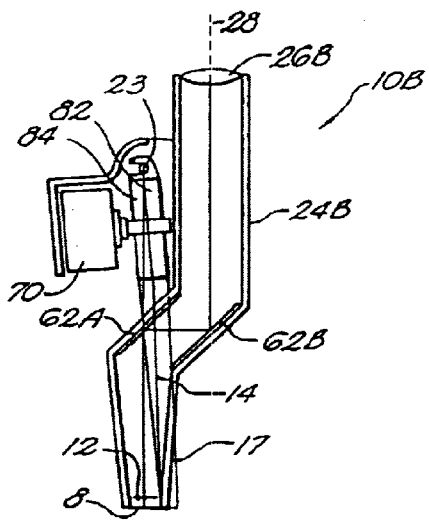
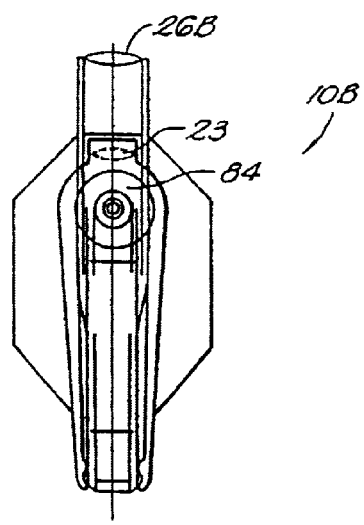
FIG. 7
FIG. 8
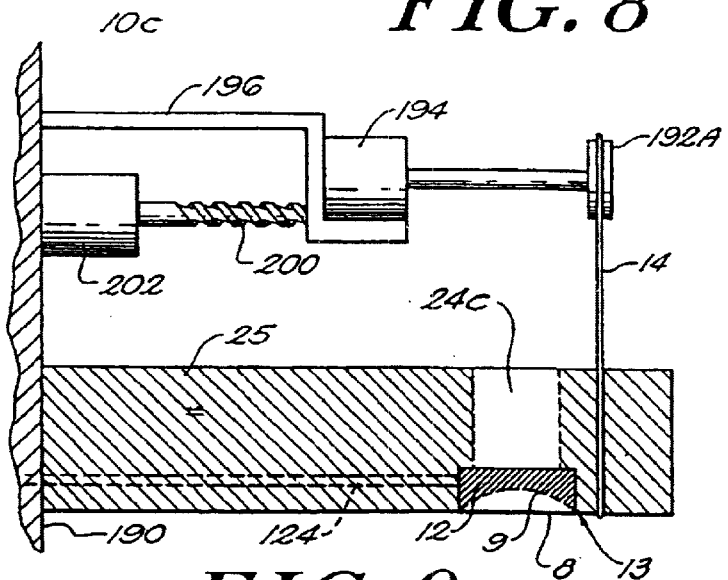
FIG. 9
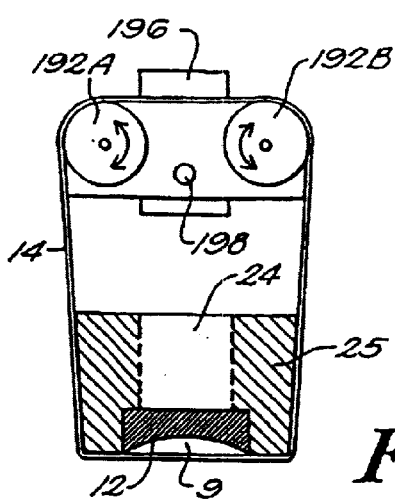
FIG. 10

SURGICAL MICROTOMES

BACKGROUND OF THE INVENTION

This invention concerns systems and apparatus for removal of biological tissue samples and, in particular, systems and apparatus for refractive vision correction.

Various techniques and devices are known in the art for the removal or slicing of thin layers of biological tissue. These instruments are generally referred to as surgical microtomes. When the instruments are specifically designed for the removal of corneal tissue they are often referred to as keratomes or micro-keratomes.

It is often desirable in the course of human therapy to remove a thin layer of biological tissue intact. This is especially true in the course of biopsying tissue specimens for the presence of cancerous or otherwise abnormal cells. For example, in the course of cancer diagnosis and/or treatment, biopsy samples are routinely taken and analyzed for the presence of cancerous cells. The thin tissue biopsies are examined microscopically as a surgical procedure is carried out to ensure that the margins of tumor excision are properly delineated and excessive excisions of healthy tissue are avoided.

Biopsies are also taken for diagnostic purposes in the course of other surgical procedures or in the course of health care, generally. For example, when a gynecological "PAP smear" test turns up a positive result for abnormal cells, cervical biopsy samples are necessary to confirm or negate the presence of cancer cells in the cervix. Biopsies are also taken in the course of various laproscopic examinations for similar purposes in order to confirm or negate the presence of abnormal or cancerous cell conditions.

The examination of biopsy samples is often a tedious process. The ability to take a standardized biopsy sample of a defined volume or thickness of tissue is highly desirous in order to facilitate either manual and automated examination of the biopsy sample. Many conventional microtomes cannot provide this standardization of biopsy samples.

Thus, there exists a need for better surgical resection instruments, generally, which can remove thin sections of biological tissue for examination purposes.

Additionally, in the field of surgical correction of refractive vision disorders, keratomes are used for various purposes. These purposes include the removal of abnormal growths in the cornea, preparation of damaged eyes for corneal transplants, preparation of eyes for other surgical procedures and direct surgical corrections of refractive disorders.

Considerable interest has been recently generated in a variety of techniques for reshaping the cornea for refractive vision correction. These techniques are based on the observation that most of an eye's refractive power is contributed by the corneal curvature itself (with the remaining refractive power being provided by the lens of the eye located inside the ocular globe). For people suffering from nearsightedness (myopia), it has been recognized that a slight flattening of the corneal curvature can correct this condition if properly applied. Conversely, correction of farsightedness (hyperopia) requires a steepening of the corneal curvature. Correction of astigmatism typically requires more complex reprofiling.

It has been suggested on a number of occasions that it is possible to correct refractive errors by mechanical sculpting of the cornea into an ideal shape and curvature. However, until very recently, there have been no tools suitable for this purpose. The anterior surface of the cornea is covered with a thin layer of epithelial tissue followed by a membrane-like structure known as Bowman's layer. Typically, Bowman's layer is about 30 micrometers thick, although it may vary from as little as 10 micrometers to over 50 micrometers in thickness.

Below Bowman's layer lies the stroma proper of the cornea. This stromal tissue is approximately 450 micrometers in thickness, although it also varies from individual to individual. Stromal tissue is composed of a highly organized matrix of acellular collagen. The Bowman's membrane which lies above it is less regular and denser.

Efforts at mechanical sculpting of the cornea have been largely unsuccessful to date because even the sharpest metal (or even diamond) blades are incapable of producing precise ablations of corneal tissue with the necessary accuracy. The irregularity of Bowman's layer is a further complicating factor which has stymied mechanical attempts at wide-area sculpting of the anterior surface of the cornea.

Attempts have been made to achieve corneal reprofiling in other ways. For example, in a procedure known as radial keratotomy (RK) the cornea is incised with radial cuts which cause the overall structure of the cornea to relax and flatten. While moderate success has been achieved with RK procedures, the result is far from ideal. In such procedures, the anterior surface of the eye contains ruts which resemble the spokes of a wheel after the incisions have healed and the actual corneal curvature is far from the ideal spherical shape that is desired. Nonetheless, millions of people suffering from refractive disorders have undergone RK procedures in the hopes of permanently correcting their vision.

In another approach, designed to avoid the complications of Bowman's layer, a thicker anterior segment of the cornea (typically including Bowman's layer and several hundred micrometers of stromal tissue) is removed, frozen and lathed on its posterior (inside) surface. This reshaped corneal cap or "lenticule" is then thawed and replanted onto the cornea. In this procedure, often referred to as keratomileusis, the integrity of the Bowman's layer is maintained but a much more invasive procedure is required to remove the corneal lamella and then reshape it in a frozen state.

In another alternative surgical procedure, a anterior segment of the cornea is again removed (or partially severed and displaced) so that the stromal bed can be mechanically reshaped (e.g. with a scalpel-like instrument). Because Bowman's layer is removed or displaced intact in such procedures, mechanical instruments (microkeratomes and the like) have had moderate success in resculpting the stroma proper. After the stromal bed has been surgically reshaped, the anterior lenticule is replaced. Again, this procedure has the advantage of avoiding mechanical shaving Bowman's layer, albeit at the expense of a deeper penetration into the stroma.

Recently, a new class of tools has become available to ophthalmologists to perform corneal surgery. This class of tools employs high energy pulses of ultraviolet radiation, typically from excimer lasers, to ablate thin layers of corneal tissue by a process known as "photodecomposition." This laser vision correction process relies upon the ability of such laser radiation to remove extremely thin layers of corneal tissue within an exposed area without thermal damage to adjacent tissue. In one type of procedure known as photorefractive keratectomy (PRK), the laser beam is either repeatedly scanned across the cornea or otherwise controlled to expose the cornea to a beam of different shape or size over time so as to effect a cumulative reprofiling of the corneal surface. In many PRK procedures, ablation is largely confined to Bowman's membrane and the laser radiation achieves very smooth and reproducible results. For patients with high dioptric errors, the ablation will also penetrate into the stromal tissue, again with typically very good results. Nonetheless, the systems and apparatus necessary for achieving laser vision correction are extremely complicated to operate and maintain.

In a particular class of PRK procedures known as Laser Assisted In Situ Keratoplasty (LASIK), a keratome is still used to remove (or hingedly displace) an anterior lenticule of the cornea (in much the same way as in the procedures that involve mechanical sculpting of the stroma) so that the laser can be used to ablate only stromal tissue. Again, like mechanical sculpting procedures, the anterior lenticule is replaced following the procedure with Bowman's membrane intact. This LASIK procedure is also very promising but likewise requires highly complex, difficult to maintain, equipment.

Conventional keratomes typically include a suction device that secures the instrument to the eye and a drive mechanism that pushes a blade through a channel within the device to sever an anterior segment of the cornea. Examples of such devices include U.S. Pat. No. 5,496,339 issued to Koepnick on Mar. 5, 1996 and European. Patent Application Pub. No. 0 771 553 by H. Schwind GmbH published May 7, 1997. The precision of these instruments is inherently limited by the clearance necessarily provided between the blade and the upper and lower surfaces of the channel. To permit the blade to pass smoothly through the instrument, the gap must be larger than the thickest portion of the blade. This constraint introduces a degree of variability that limited the instrument's utility particularly in achieving specific refractive corrections.

There exists a need for alternative techniques in order to reprofile the cornea. Simple mechanical devices that could achieve the desired degree of accuracy, especially in shaping Bowman's membrane tissue as well as stromal tissue, would satisfy a long-felt need in the ophthalmic community.

Moreover, there exists a need for better keratomes, generally, to facilitate both mechanical and laser vision correction procedures. A better, more accurate keratome, would allow ophthalmic surgeons to perform therapeutic keratectomies (removing small regions of corneal tissue which exhibit abnormal growths or ulcers), resections of anterior corneal segments (as a first step in keratomileusis, stromal sculpting procedures, LASIK procedures and the like) and a variety of other surgical operations on the cornea.

SUMMARY OF THE INVENTION

Methods and apparatus are disclosed for removal of biological tissue slices or layers, for example, in the form of lamellar sections of a defined shape and thickness, employing a reference member that engages a target tissue site and cooperates with a cutter to remove the tissue segment or lamella. The cutter preferably includes a flexible cutting element such as a wire or band element that is brought into physical contact with a guiding edge of the reference member and then draw along a path defined by the guide edge through the tissue in order to sever, at least partially, a tissue section.

In one particularly useful aspect of the invention, methods and apparatus for keratectomy are disclosed employing an ocular reference member that engages the upper central region of the cornea and cooperates with a cutter to remove a lamellar segment from the cornea. Such lamellar resections are useful in preparing the cornea for further surgery (by mechanical or laser surgical techniques), or in performing refractive keratectomy directly upon the eye, or in treating (e.g., smoothing) the corneal surface to correct abnormalities, (e.g., to remove ulcerated tissue or otherwise improve the optical properties of the cornea).

Various structures can be used as cutters in the present invention, including flexible cutting elements such as wires, fibers, bands and the like. A driver is preferably employed to bring the cutter into physical contact with a the guiding edge of the reference member and then draw the cutter along the guiding edge and through the tissue. Exemplary driver mechanisms including motors which activate a sweeping motion, linear motive actuators, translating stages, pivoting actuators and rotating actuators.

The cutter preferably also moves in a linear direction (e.g. in a direction orthogonal to the path along which the cutter is drawn through the tissue) as it slices a lamella. This linear motion can be unidirectional or oscillatory.

In another embodiment of the invention the cutter can be a relatively rigid element (e.g. a very thin, sharply beveled blade) that likewise is drawn across a guiding edge of an ocular reference member to effect tissue resection. The blade can be connected to a wire, fiber, band or belt and its movement can be actuated by the same mechanisms as described above with flexible cutting elements. So long as the ocular reference member is incorporated into a flat support base that is flush with reference member (or subsumes the function of the guiding edge), the blade as it is drawn The guiding edge of the reference member defines a path through the tissue. The shape of the cavity and the geometry of the guiding edge define the shape of the sliced lamella. Because the cutter can be flexible or driven by a flexible driver assembly, the edging need not be planar and, in some applications, a non-planar guiding edge is desirable (to remove non-uniform tissue samples or, in the case or refractive surgery, to effect astigmatic corrections).

The invention can be used in refractive surgery either as a reprofiling device or, more simply, as a microkeratome to perform initial processing steps in order to prepare the cornea for mechanical sculpting or LASIK procedures. In refractive procedures, the reference member can have a distal end that defines a cavity of predetermined shape in order to capture a desired volume of tissue. When the cutter is drawn through the corneal tissue, the tissue within the cavity of the reference member is severed from the cornea. By proper choice of the cavity geometry, a new curvature will be imparted to the remaining corneal tissue. For example, a concave cavity will remove a volume of tissue that results in an overall flattening of the corneal curvature, thus correcting myopic vision errors. Other designs of the distal end can yield hyperopic and/or astigmatic corrections.

Moreover, the present invention can be used in mechanical sculpting procedures for dual purposes: first, to remove (or hingedly displace) an anterior portion of the cornea (with the epithelium and/or Bowman's layer of the central optical zone unaltered) and then in a second step to reshape the overall curvature by removing a defined volume of corneal stroma tissue. After the lamella is removed from the stroma, the anterior "cap" can then be replaced over the sculpted region.

The guiding edge of the reference member need not define a planar path for the cutter. In fact, the guiding edge can be a non-planar shape in some applications, such as in reprofiling corneal tissue to correct astigmatisms. The ability to perform non-planar resections is an important advantage of the present invention. Resections of tissue with convention microtome and microkeratome device are limited to planar slices because of the inherent geometry of knife blades and the like as cutting elements. When a non-planar edge is incorporated into the reference member, it is also desirable in certain applications to also have an orientation marker for orienting the cutter and the reference member such that the path that the cutter follows through the tissue is defined and fixed. It is also desirable to include means for adjusting the orientation so that the user can select a particular azimuthal orientation.

In one embodiment of the invention, the reference member and cutter are joined by a pivot bearing and a driver causes the cutter element (e.g. a moving wire) to swing into engagement with the guiding edge of the reference member. The driver continues to draw the cutter through the tissue until the lamella is severed (or until a stop point is reached). The moving wire or band can be reeled in either a linear or oscillating fashion by one or more reel or spool mechanisms. The cutter element and the spools which facilitated the motion of the cutter can be designed as a disposable cartridge which is replaced with a new unit following each procedure.

The reference member can be hollow with a transparent distal end to serve as a viewing tube. The proximal end can include an eyepiece. The reference member can straight or folded (with internal mirrors) to permit viewing of the tissue section. Such viewing is particularly desirable in corneal resection procedures where the lamella to be removed or displaced is usually centered in the optical zone (or aligned with the pupil but offset nasally). The reference member can also include one or more means for securing the tissue segment including, for example, suction ports incorporated into the periphery or the cavity of the reference member, adhesive coatings, or mechanical means, such pins, teeth, or clamps. Alternatively a separate suction ring or other securement structure can be used in conjunction with the reference member.

The term "cutter" as used herein is intended to encompass any one of a a variety of cutting elements that can be drawn through biological tissue to effect a partial or complete resection of a tissue segment. It is often desirable that the cutters of the present invention are preferably flexible elements such that physical contact between the cutter and the guiding edge of the reference member ensures precise removal of a predictable, defined volume of tissue. However, in other applications a stiff blade-like structure can also be used advantageously. The term "guiding edge" is used herein to describe that portion of the reference member that interacts with the cutter to guide the cutter thorough the tissue. The term "cavity" is used herein to describe the shape of the distal end of the reference member such that the form of the cavity defines, at least in part, the volume of tissue removed. The term "removed" is intended to encompass not only the complete severing of a tissue lamella but also the partial resection of such tissue, including procedures in which a lamella is partially severed and hingedly displaced for subsequent reattachment. The terms "lamella" and "lamellar segment" are used herein to describe the tissue segment removed by the action of the cutter; such lamella need not be flat (and in most instances it is not flat). The term "adhesion" is intended to encompass both frictionally adherent and adhesively bonded mechanisms for securing the reference member to the target tissue site.

BRIEF DESCRIPTION OF THE DRAWINGS

FIG. 4 is a top view of the cutter assembly of FIGS. 2 and 3;

FIG. 5 is a bottom view of the cutter assembly of FIG. 4 including the disposable cartridge;

FIG. 6 is a side view of another apparatus according to the invention (employing a folded viewing tube), again shown in a non-engaged position;

FIG. 7 is another side view of the apparatus of FIG. 6 showing the cutter element and reference member engaged with each other;

FIG. 8 is a top view of the cutter assembly of the apparatus of FIGS. 6 and 7;

FIG. 9 is a partially cross-sectional side view of another apparatus according to the invention (employing a horizontal support base as a receptacle for the ocular reference member);

FIG. 10 is a partially cross-sectional front view of the apparatus of FIG. 9;

In FIG. 24A, a first step is shown, involving the removal of a portion of the cornea is shown;

FIG. 24B shows the second step in this procedure where the posterior surface of the removed segment of corneal tissue is reprofiled;

FIG. 24C illustrates the third step in the procedure of whereby the reshaped corneal segment is replanted onto the cornea;

In FIG. 25A a portion of the cornea is again removed (or hingedly displaced) employing the present invention;

In FIG. 25B a second reprofiling procedure is carried out on the exposed corneal surface;

In FIG. 25C, the removed or displaced tissue segment is replanted onto the cornea;

FIG. 27 is a side view of a reference member coupled to a vacuum or suction means; FIG. 28A is a bottom view of a reference showing member showing one configuration of suction ports; and FIG. 28B is another bottom view with an alternative configuration of suction ports.

DETAILED DESCRIPTION

Figure 1:
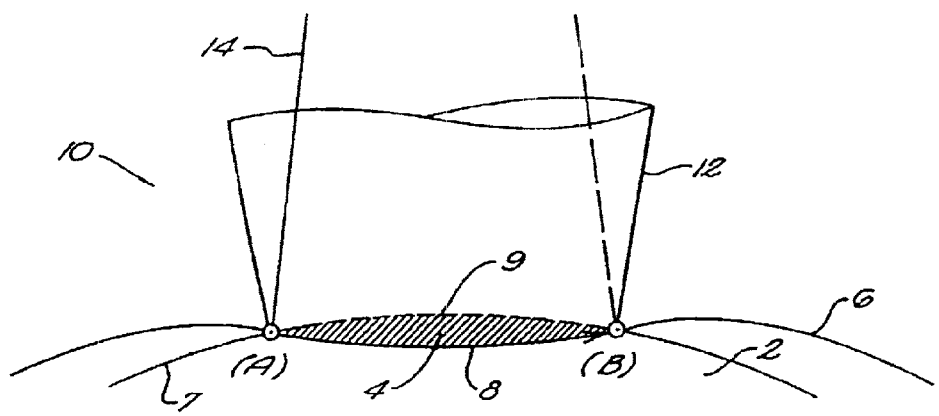
FIG. 1 is a schematic illustration of a system according to the invention for removal of a thin layer or lamella of biological tissue.

In FIG. 1, a system 10 according to the invention is shown schematically disposed upon the surface of a biological tissue site 2 for removal of a lamella 4. In one embodiment, the tissue 2 is either the anterior surface of the cornea or an exposed region of the cornea and the removed lamella is chosen such that the overall curvature of the cornea is modified in order to correct refractive errors in vision. The simplified schematic illustration of FIG. 1 shows the system 10 as comprising two fundamental components: a cutting element 14 for slicing a lamellar segment from the tissue along a cutting surface, and a reference member 12 for holding a portion of the surface in place as it is cut. The reference member 12 is adapted to engage the tissue surface and has a peripheral, guiding edge 8 for guiding the cutter 14 along a cutting surface.

The cutter 14 of FIG. 1 can be a wire, fiber, band or blade cutting element which cooperates with the reference member 12 to remove a lamella of tissue from the surface. The cutter 14 is guided long surface 8 and, thereby, drawn through the tissue (from points A to B as shown schematically in FIG. 1) to effect removal of the lamellar segment of tissue. (In use, particularly during corneal surgery, the surface may be deformed—as shown by line 6—as a result of contact between the reference member 12 and the tissue 2. Following surgery, the surface will return to its original curvature—as shown by line 7—except as modified by the removed lamella.)

Figure 2:
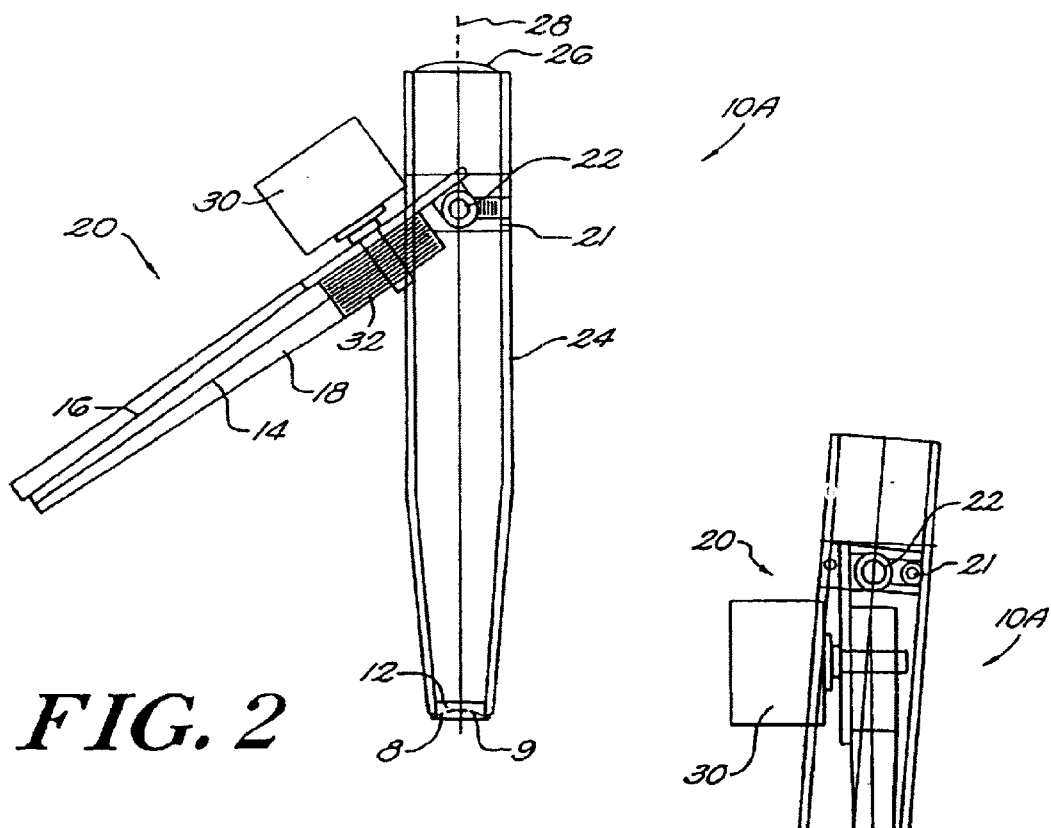
FIG. 2 is a more detailed schematic side view of an apparatus according to the invention shown in an initial position in which the cutting element is not yet engaged with the guiding surface of the reference member.

In FIG. 2, a more detailed apparatus 10A is shown for implementation of the present invention. The apparatus of FIG. 2 can be particularly useful in performing refractive keratectomy. System 10A includes a rigid reference member 12 at the distal end from a viewing tube 24. An eye piece 26 at the proximal end of viewing tube 24 facilitates viewing of the cornea along sight line 28. The eyepiece can also include crosshairs or vernier marks to aid in positioning of the reference member. The assembly 10A further includes a pivot bearing 22 which connects a cutter assembly 20 with the viewing tube 24. The pivot bearing 22 can be secured to the viewing tube 24 by a marker band 21 which permits adjustment of the azimuthal orientation of the cutter assembly 20 relative to the reference member 12.

The cutter assembly 20 of FIG. 2 includes a platform 16 (connected via pivot bearing 22 to the viewing tube 24) and a cutter cartridge 18 disposed upon the platform 16. As shown, the cutter cartridge includes at least one reel or spool 32 which carries the cutter 14 (e.g., a wire or fiber). The cutter assembly can further include a spool motor 30 which serves to rapidly pull the wire in a linear (unidirectional or oscillating) direction orthogonal to the cutting path as it is being drawn along the guiding edge of reference member 12. As shown in FIG. 2, the cutting assembly 20 has been swung up and out of engagement with reference member 12. This is a typical initial position for the system. In use, the cutter assembly swings downward in a pendulum fashion, pivoting about bearing 22 until the cutter 14 engages the guiding surface 8 of reference member 12.

The reference member 12 of FIG. 2 is a solid structure, and preferably at least partially transparent to facilitate viewing through viewing tube 24. The peripheral edge of the reference member defines a cutting path for the cutter 14 when these components are brought into engagement. The reference member 12 further includes an internal cavity 9 which will define the shape of the removed lamella. Because the cutting element 14 is rapidly moving in a linear direction as it traverses the path defined by the edge 8, it is important that the edge material of reference member 12 be very hard and resistant to damage by the cutting element. For this reason, the edge of the reference member is preferably formed of a ceramic material or otherwise hardened material. In some applications a diamond or sapphire ring structure may be desirable. Alternatively, plastic materials coated with diamond-like protective layers can be employed. It may also be desirable to impart a degree of adhesiveness between the bottom (e.g. the cavity portion 9) of the reference member and the cornea by an appropriate coating prior to contact or by creating a frictional adhesion between the bottom of the reference member 12 and the tissue.

Figure 3:
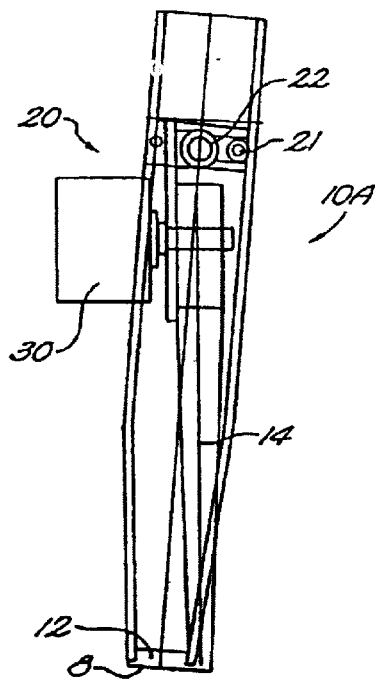
FIG. 3 is another side view of the apparatus of FIG. 2 showing the cutting element and guiding surface engaged with each other.

In FIG. 3, the system 10A is again shown in side view with the cutting assembly 20 fully engaged with the reference member 12. As shown in FIG. 3, cutter 14 has been drawn completely across the guiding edge 8 of reference member 12. Motor 30 preferably imparts a linear motion to the cutter element during the entire time during which it is contact with the tissue surface and is being drawn along edge 8.

In FIG. 4, a top view of the cutter assembly 20 is shown. Spool 32 and cutter wire 14 are shown in phantom is so far as they would be disposed beneath the cutter platform 16 in this view. As shown, the cutter assembly further includes pivot bearings 22A and 22B which connect the cutter assembly to the viewing tube 24. The pivoting action of the platform vis-à-vis tube 24 can be actuated by drive motor 34 (or similar devices) under manual or automated control. Also shown in FIG. 4 is spool motor 30 which pulls the cutter wire 14 and causes it to unroll from spool 32 and past along the guiding edge 18 of reference member 12. Additionally shown in FIG. 4 is a guillotine mechanism 38 which can be activated at the completion of the operation to sever the cutting wire 14. The guillotine mechanism 38 can be a knife-edged tool or a similar mechanism which simply serves to sever the cutting element upon completion of the operation, such that the motor 30 causes the severed wire (or similar cutting element) 14 to be wound completely upon the take up reel or spool 54.

In FIG. 5, a bottom view of tie cutter assembly 20 is shown including a cartridge 18, typically constructed to be disposable. The cartridge 18 is mounted upon platform 16. Cartridge 18 can include a feed reel or spool 52 about which the cutter wire 14 initially is wound and a take up spool 54. The cutter wire 14 is wound from the first spool 52 past a set of ferules 58A, 58B to the take up reel or spool 54. One or more tensioning posts 56 can also be employed to ensure the proper tension.

The ferules 58A, 58B serve as guide posts for the cutting element 14 as it is drawn along the guiding edge of the reference member. These ferules can also provide snap in attachment points for joining the cartridge 18 to the platform 16. One or more additional snap-on projections (not shown) can also be included in the cartridge body to provide a secure connection between the cartridge 18 and the platform 16 during usage. The guide posts 58a, 58b which serve as conduits for the cutter element 14 are preferably formed of a ceramic or otherwise hard material. Most of the other components of the cartridge can be constructed of inexpensive plastic. (Alternatively, the entire cutter assembly can be constructed so as to be disposable with a snap-on/snap-off connection to the reference member and/or drive mechanism.)

The cutting element 14 can be a wire or band formed from metal, ceramic, or other sufficiently high tensile strength materials. For example, a cutter element can be a tungsten or steel wire having a diameter of about 1 to about 25 microns. Alternatively, the cutter element can be a carbon, silicon carbide or ceramic fiber of similar dimensions. The cutting element can be a monofilament or a multifilament structure. In some applications a smooth fiber will be desired while in other instances a braided or otherwise textured wire surface will be desired to induce a tearing action. Although round wires are most readily available, other shapes including elliptical or flat (ribbon-like) structures may be desirable. The texture of the wire can be modified by abrasion or coating to achieve the appropriate surface friction during cleavage of the lamellar segment from the tissue surface.

Also shown in FIG. 5 are two additional wire guides 60A and 60B which serve to position the wire in such a way that it can be severed by guillotine mechanism 38 (described in connection with FIG. 4). The guides 60A and 60B, like the tip ferules 58A and 58B, are preferably constructed from a ceramic or similarly hard material to withstand constant physical contact with the cutter element 14.

It should be noted that although the apparatus of FIGS. 2–5 is shown with two spools 52, 54 and a cutting element 14 that is wound end-to-end between the two spools, it is also possible to employ the cutting element 14 as a continuous loop using either one or two spools for transport.

Although tensioning posts 56 are illustrated in the embodiment of FIGS. 2–5, it should be clear that various other mechanisms can be employed to ensure proper tension of the cutting element 14 as it is drawn along the guiding edge 8 of reference member 12. Proper tension is dependent upon a number of factors including the tensile strength of the cutting element 14, its diameter, its texture (e.g., flat, smooth, abraded or roughened), the linear speed of the wire (as it is drawn from one spool to another), and the speed that the cutting element as it traverses the path. Tension can be controlled by the speed of the spool motor 30, the resistance of the take-up spool 54, similar resistance by the feed spool 52 (e.g., by preloading the wire under tension), by mechanical brakes or electronic brakes (e.g., eddy current controllers). In some applications it may be desirable to impart a non-uniform tension to the wire during the course of the procedure. Similar variations in tension may also be desirable when the cutting element is operated in an oscillating rather than unidirectional manner.

Although two separate motors 30 and 34 are shown in the embodiment of FIGS. 2–5 for actuating the take-up spool and pivot bearings, respectively, a single motor can be used for both purposes. The driver that brings the cutter into engagement with the reference member (and the tissue) can also be manual powered. The driver need not employ a pivoting or sweeping action; translatory stages can be substituted for illustrated driver mechanisms. Moreover, in some applications, it may also be desirable to provide an additional degree of freedom in the movement of the wire of the cutting element 14 as it traverses the cutting path. For example, instead of a translatory motion along the guiding edge 8, the cutting element 14 can be rotated in a sweeping motion as it is drawn across the corneal tissue surface. Various driver mechanisms can be used to impart such a spinning motion, including a spinning motor or simply the incorporation of a post into the reference member to prevent one side of the wire from traversing the path and, thereby, converting translatory motion into a pivoting action of the cutting element 14 about such post.

In FIGS. 6–8 another embodiment of the invention is illustrated in which both the feed and take-up spools are mounted on a single axis. In FIG. 6, the system 10b is shown including a cutter assembly 20B and a viewing tube 24B. Like the previous embodiment, the viewing tube 24 includes a reference member 12 and a guiding edge 8 at its distal end. Viewing 24 is shown in a folded configuration (so that pivot 23 is disposed directly above the center of the reference member).

Because the viewing tube 24B of FIGS. 6–8 is folded, mirrors 62A and 62B are provided to facilitate viewing of the surface undergoing resection. To compensate for any defocusing as a result of the longer optical path, an eye piece with a lens 26A can be incorporated into the proximal end of the instrument so that the user can have a clear image of the tissue surface along sight line 28.

In FIG. 6, the instrument is shown in an initial position in which the cutting assembly 20B is swung up and out of engagement with the reference member 12. In FIG. 7, the apparatus is shown with the cutting assembly and reference member fully engaged with each other such that the cutting element 14 has traversed a path along the guiding edge 8.

As further shown in FIGS. 6–8, the cutting assembly includes at least one motor 70 for actuation of the take-up spool 84, and preferably also actuating the pivot bearing 23. Upon actuation of the take-up spool 84, the cutting element 14 can be drawn from the feed spool 82 along a path from ferule 58A to ferule 58B and taken up by spool 84. As the wire is drawn between the two ferules 58A, 58B, the moving cutter is driven into engagement with the guiding edge 8 of reference member 12 to perform the tissue resection. System 10B includes an alternative mechanism for adjusting the azimuthal orientation of the reference member relative to the cutter assembly 20B. The distal portion of the viewing tube 24 B (including reference member 12) is mounting on a rotatable marker sleeve 17 which can be turned to any desired orientation.

In FIGS. 9 and 10 a further embodiment of the invention is illustrated in which a generally horizontal support base 25 replaces the vertical viewing tube of the previous embodiments. (It should be appreciated that the terms "vertical and "horizontal" are used solely for ease of illustration; in practice, the orientation of a patient and the ocular reference member as well as the supporting structures can take various inclinations.) The support base 25 can include a hollow cavity 24C which can serve the same function as the viewing tubes described above. This hollow cavity is also adapted to include a receptacle 13 for the reference member 12. Like the previous embodiment, the reference member 12 includes an inner surface 9 and a guiding edge 8.

As further shown in FIGS. 9 and 10 the cutter 14 can be a flexible fiber or band element which is driven or oscillated in at least one linear direction traverse to the lower surface of support base 25. This can be accomplished by another reel mechanism (pulley wheels 192A and 192B) at least one of which can be driven by a motor 194. The motor and cutting element oscillating mechanism can be connecting to a rigid post 190 (or other relatively fixed orientation structure) via flange 196. This flange and the associated elements (including the cutter 14, itself) can be drawn in a second (typically, but not necessarily, orthogonal) direction so as to traverse the guiding edge 8 of the reference member 12. One mechanism to impart such linear motion shown in these figures is a worm gear 198 coupled to a screw 200 driven by motor 210. As with the previous illustrations, the moving cutter 14 is driven into engagement with the guiding edge 8 of the reference member 12 to perform partial or complete tissue resection.

Figure 11:
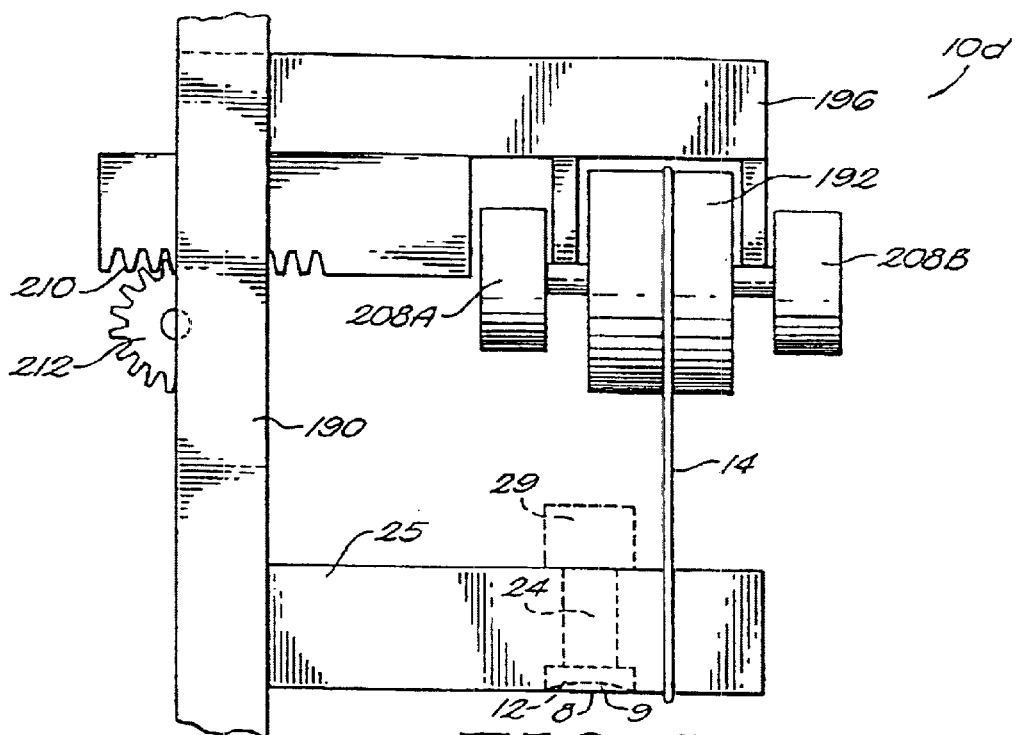
FIG. 11 is a partially cross-sectional side view of another apparatus according to the invention.
Figure 12:
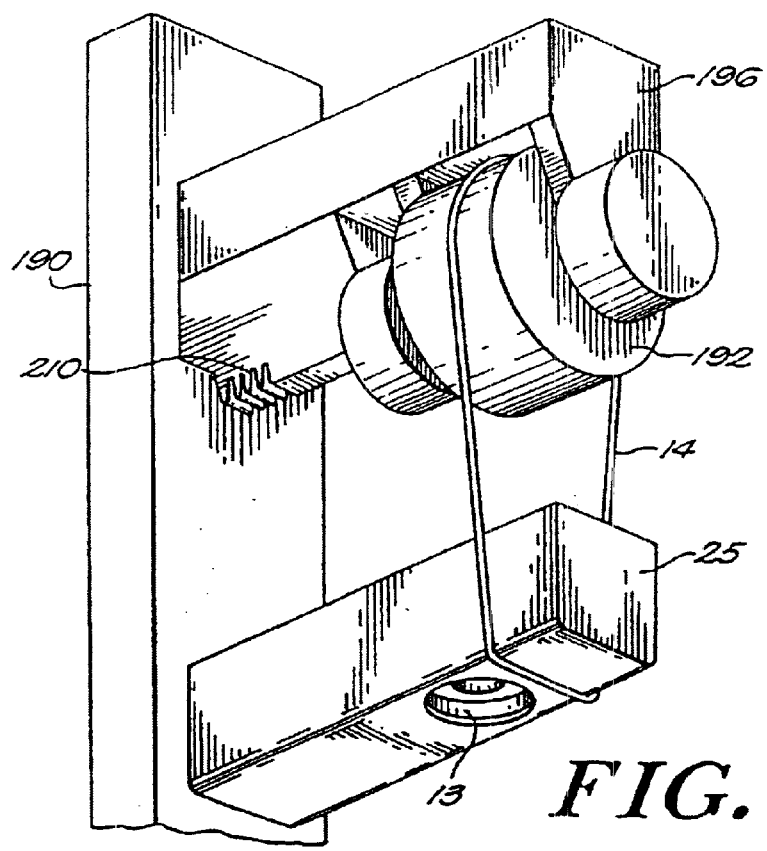
FIG. 12 is a schematic perspective view of the apparatus of FIG. 11.

In FIGS. 11 and 12, yet another embodiment of the invention is illustrated. In this embodiment the fiber or band cutter 14 is drawn across the guiding edge 8 of the reference member 12 in a manner nearly identical to that described above in connection with FIGS. 9 and 10. However, a single reel or drive wheel 192 is used to impart the linear or oscillating motion to the cutter. The drive wheel 192 can be activated by a motor (not shown) and can further be coupled to counter balanced weights 208A and 208B to dampen vibrations. In the embodiment of FIGS. 11 and 12, a rack 210 and pinion 212 assembly is used to impart linear motion to the cutter 14 to draw it across the guiding edge 8 of reference member 12. Again, the support base 25 can include a viewing tube 24 to facilitate viewing of the procedure. However, because the assembly as shown blocks direct vertical viewing, folding mirrors such as those illustrated in FIGS. 6 and 7) can be employed to redirect an image of the tissue undergoing resection to remote optics. Alternatively, the viewing port 24 can be equipped with an optional video camera assembly 29 for electronic imaging and/or record-keeping.

Figure 13:
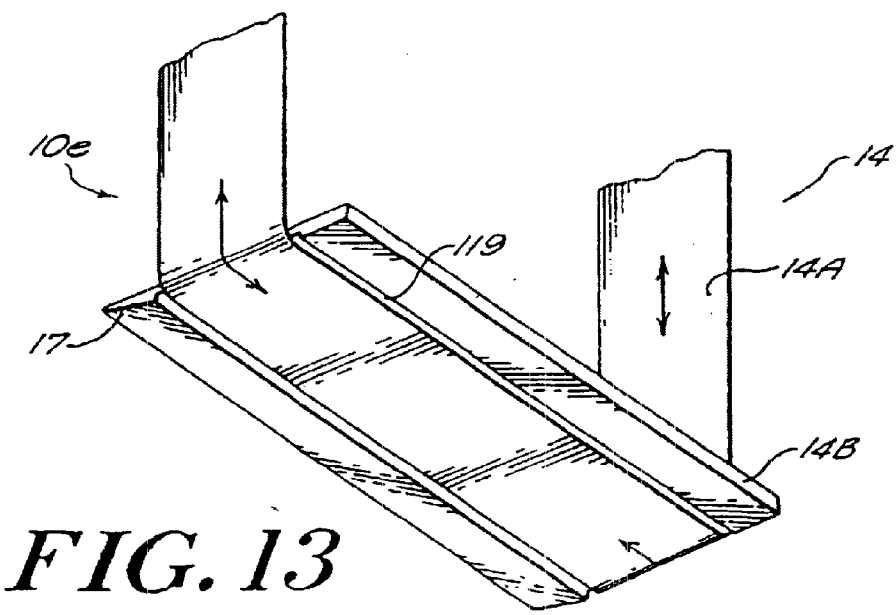
FIG. 13 is a schematic perspective view of an alternative cutter element for use in the present invention.
Figure 14:
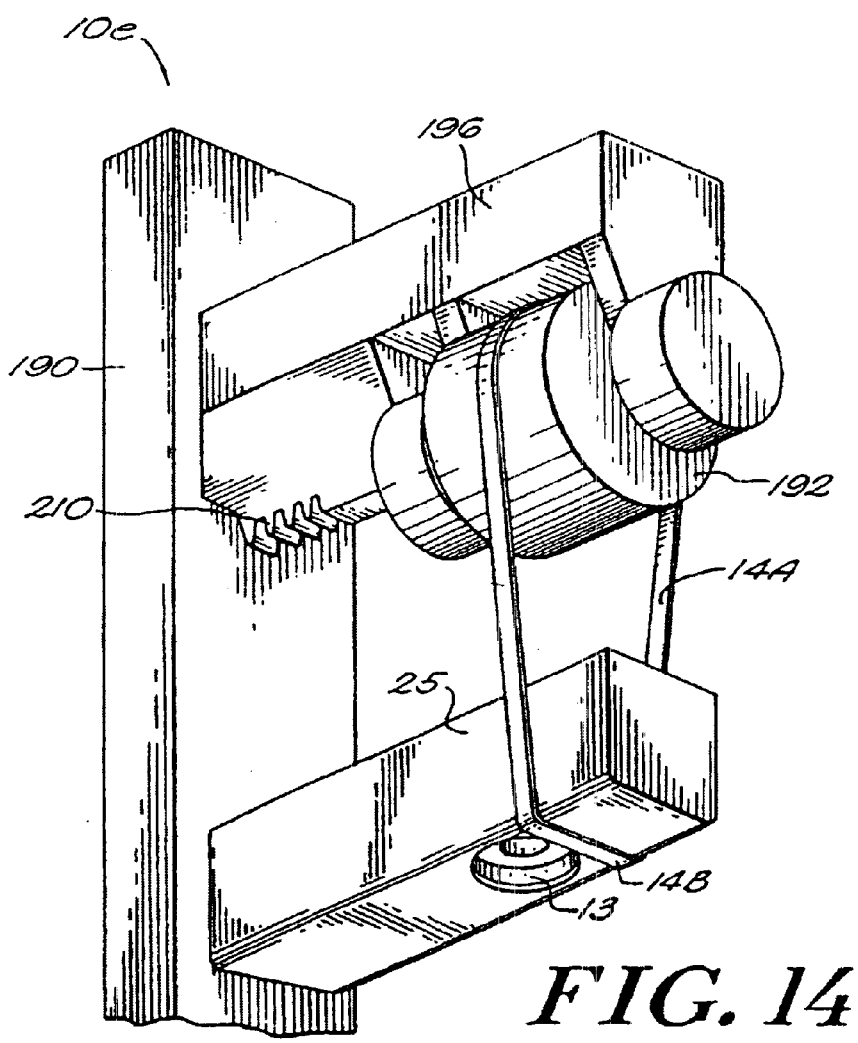
FIG. 14 is a schematic perspective view of an apparatus according to the invention, employing the cutter element of FIG. 13.

In FIGS. 13 and 14, another embodiment of the cutter element 14 is shown. In this embodiment the cutter element 14 comprises two elements: a flexible band element 14A and a blade element 1 4B which is at least stiff over a portion of its length. The blade element preferably includes a single beveled sharp edge on at least one face as illustrated at edge 17. The word "blade" as used herein is intended to encompass unitary structures and composite structures having at least one relatively stiff component designed to cut tissue. The blade element 14B can further include a recess 19 which receives the moving belt 14A. When bonded together, belt 14A can be utilized to cause the blade 14B to oscillate back and forth along the bottom surface of the support base 25 (as shown more clearly in perspective view FIG. 14). The illustration in FIG. 14 is otherwise practically the same as that shown in FIG. 12 and operates in the same manner to cause the cutter to move back and forth as it is drawn across the guiding edge of the reference member. Preferably, the blade 14B is made of a high strength material such as stainless steel and sharpened to a blade angle where the radius of curvature at the tip of the blade is less than about 500 nanometers. Suitable blades are available from various commercial sources such as American Cutting Edge, Inc., (Centerville, Ohio) or Insight Technologies Instruments, LLC, (Milford, Conn.).

The blade 14B of FIGS. 13–14, in one preferred embodiment, can be made of a magnetically susceptible material and the support body 25 can include one or more magnetic elements (e.g. permanent magnets or electromagnets) that cause the blade 24 to remain flat and well secured as it is oscillated and drawn across the ocular reference member. Alternatively, the blade can be magnetized and attracted to a magnetically permeable material within the support body.

Figure 15:
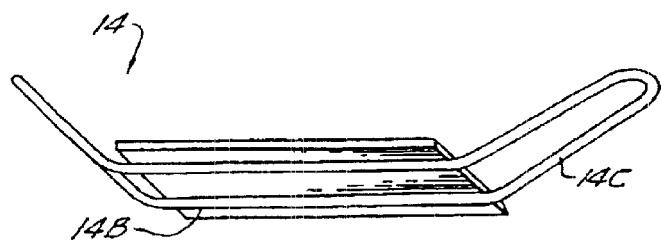
FIG. 15 is a schematic perspective view of another alternative cutter element for use in the present invention.
Figure 16:
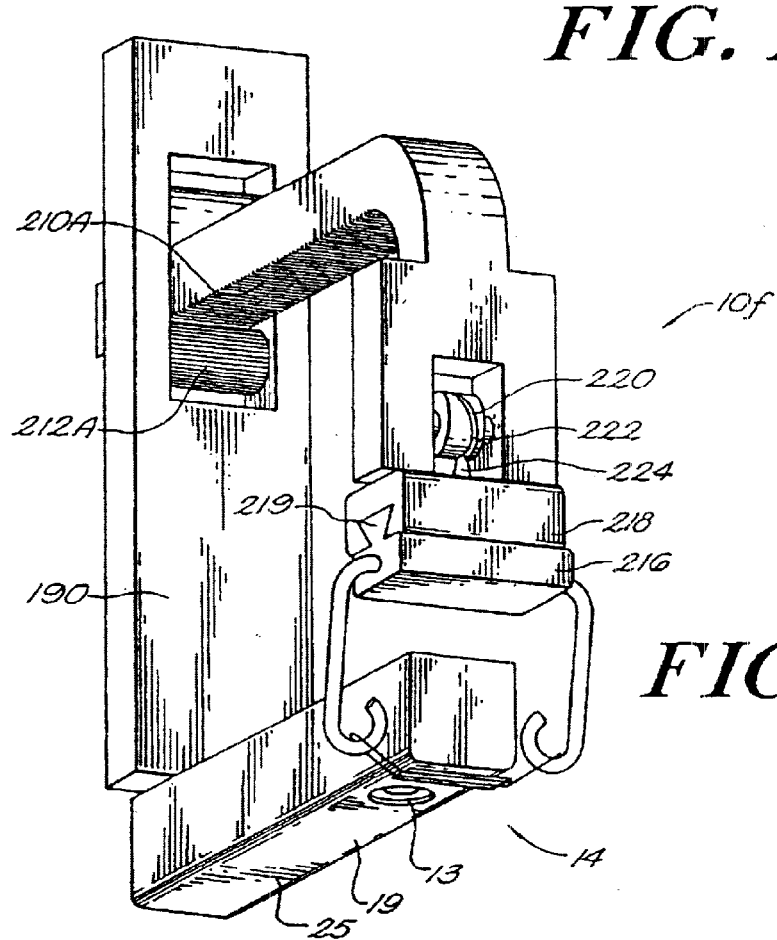
FIG. 16 is a schematic perspective view of an apparatus according to the invention, employing the cutter element of FIG. 15.

With reference to FIGS. 15–16, yet another embodiment of the invention is shown in which the cutting element 14 comprises a blade 14B and one or more supports 14C. The supports can be either wires or more rigid strut-like components. In either event, the support struts 14c can be bonded to the blade 14B to facilitate oscillatory motion.

In FIG. 16, an overall system 10F is shown in which the Blade 14B is connected to a support to FIG. 16. This support includes a upwardly projecting coupling post 224 and at least one rail element 217 which is coupled to a linear track 218 for back-and-forth motion. Although various alternative techniques will be obvious to the skilled artisan, the mechanism illustrated in FIG. 16 employs an oscillation wheel 220 having an undulating track in which the coupling pin 214 is carried. As the wheel 220 rotates, the pin 224 moves back-and-forth causing the rail 219, support 216 and, ultimately, the blade 14 to likewise move back-and-forth along the lower surface 19 of support body 25.

As in previous figures, the blade is drawn across the cornea by a linear actuating mechanism which is again illustrated schematically as a rack and pinion gear set.

Figure 17:
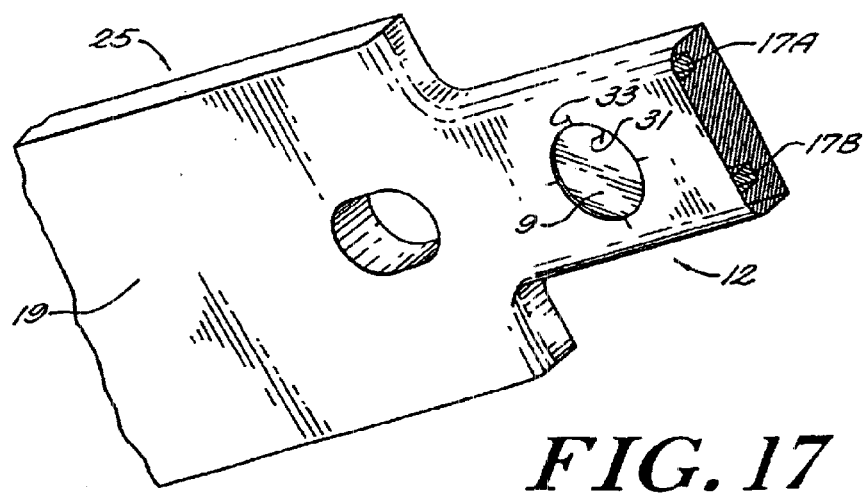
FIG. 17 is a schematic, partially cut-away, perspective bottom view of a support base and ocular reference member according to the invention.

In FIG. 17, a perspective, partially cross-sectional view of the bottom surface of a support base 25 is illustrated. As shown, a reference member 12 having a corneal engaging surface 9 has been fitted into a receptacle in the base 25. The reference member 12 can have at least one azimuthal reference marker 31 that can be aligned with at least one azimuthal orientation marker 33 on the base.

The width of the support base in the vicinity of the reference member 12 is preferably somewhat longer than the length of the blade which traverses it so that the oscillatory (back-and-forth) motion can be completely carried out with the blade held firmly to the lower surface 19 of the base 25. The blade, if it is made of a magnetically susceptible material, can be further constrained against any forces that might otherwise cause it to bow or shimmy by implanting one or more magnets (such as bar magnets 17A and 17B) into the base.

Figure 18:
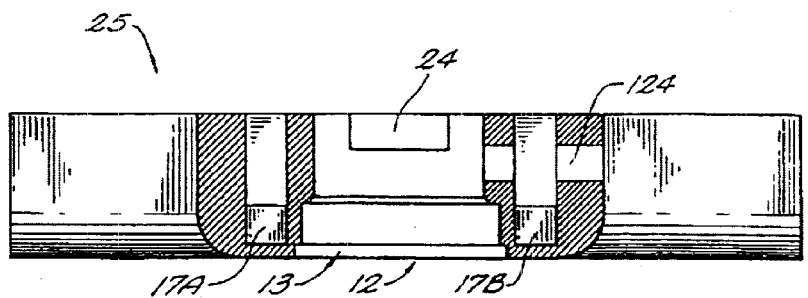
FIG. 18 is a schematic cross-sectional view of the structural component of the support base of FIG. 17.

The configuration of these magnets is shown more clearly in the cross-sectional front view of the support base presented in FIG. 18. As shown, the base includes a receptacle 13 into which is fitted an ocular referencing member 12.

Likewise magnets 17A and 17B are incorporated into the body of base 25. The base can further include a hollow viewing tube directly above the reference member 12 to facilitate real-time monitoring of the procedure.

FIG. 18 also shows a suction source 24 which provides a degree of vacuum to the backside of the reference member. If the reference member 12 is porous, the vacuum provided by vacuum source 112 will draw that portion of the epithelium or cornea which is targeted for excision into the cavity of the reference member.

Various porous materials can be used to construct the reference member 12. In one preferred embodiment, the reference member is both porous and transparent. For this purpose, plastics with many holes can be used. Alternatively, porous sintered plastic filters available from commercial sources, such as Millipore Corporation, (Bedford, Mass.) can be employed as transparent reference members. Porous plastics can also be manufactured by compression molding techniques.

It has further been found that water enhances the transparency of such porous plastic reference members because when the pores are filled with water (with an index of refraction of about 1.35) it closely matches the index of refraction of the plastic matrix material (typically having an index of about 1.5). Preferably the average pore size of the reference member ranges from about 1 nanometer to about 50 micrometersm, and more preferably from about 100 nanometers to about 5 micrometers. Such porous structures readily permit a vacuum source to draw the target tissue into the cavity of the reference member and firmly hold it during excision.

Another class of materials that are useful in constructing reference members are porous glasses, such as the VICOR™ glass manufactured by the Corning Glass Company (New York, N.Y.). Such porous glass materials can in some instances act as attachment mechanisms without a vacuum source as a result of the natural vacuum created by capillary forces when the glass comes in contact with a tissue segment, especially wet tissue surface. Other materials that exhibit such capillary action can likewise be useful.

A third means of adhesion is to provide the inner surface of the reference member with an abrasive coating (e.g., by spray coating a silicon oxide or silicon carbide coating onto the surface). In this embodiment, a vacuum source need only be applied to a small portion of the inner surface of the reference member (such as along a peripheral rim). The abrasive coating forms a network of "micro canyons" which allow the vacuum source to exert suction along a substantial portion, if not all, of the inner surface.

In lieu of vacuum and capillary sources, other techniques such as the application of ophthalmic glues can be employed instead.

Figure 19:
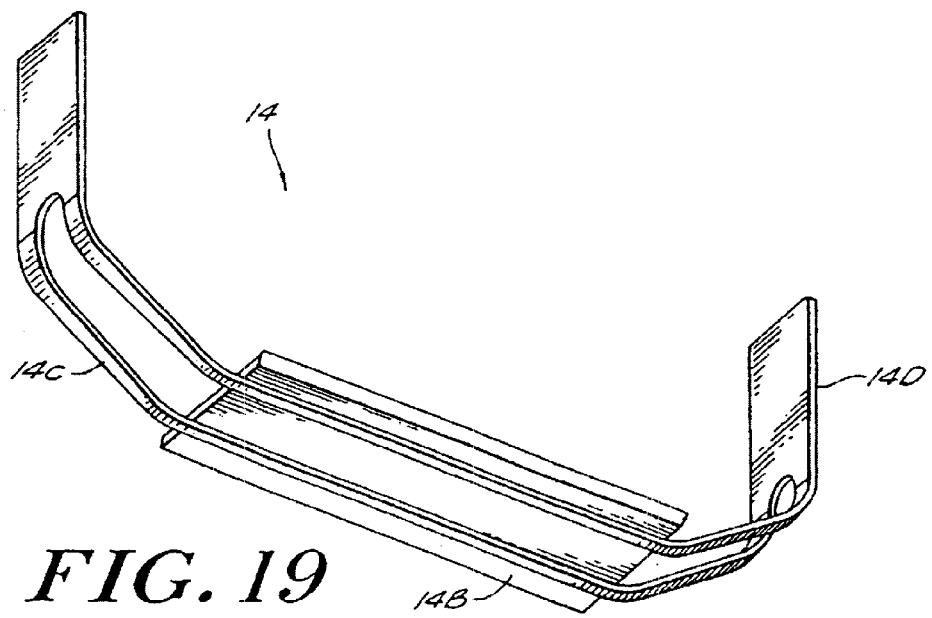
FIG. 19 is a schematic perspective view of an alternative cutter element for use in the present invention.
Figure 20:
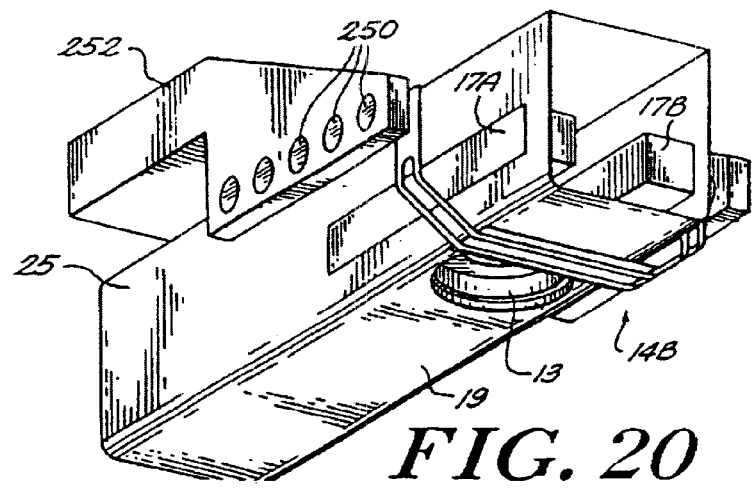
FIG. 20 is a schematic perspective view of an apparatus according to the invention, employing the cutter element of FIG. 19.
Figure 21:
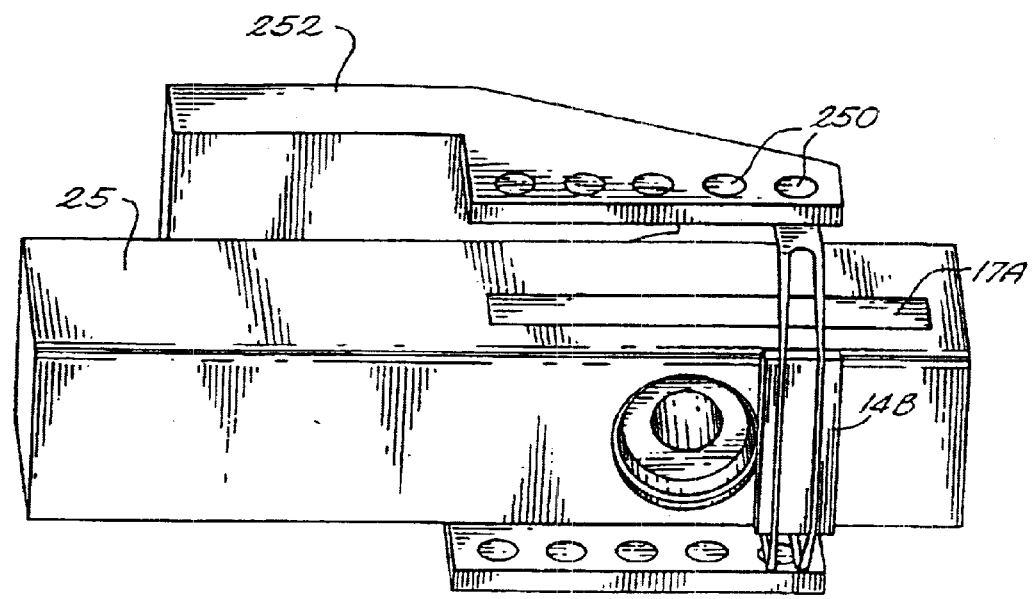
FIG. 21 is another schematic perspective view of an apparatus according to the invention, employing the cutter element of FIG. 19.

In FIGS. 19–21 yet a further embodiment of the invention is shown in which the cutter 14 includes not only a blade 14B and support struts 14C but also flanges 14D of magnetically permeable material. As further illustrated in the prospective front and bottom views of FIGS. 20 and 21, respectively, the blade is held firmly to the bottom 19 of the support 25 by embedded magnets 17A and 17B, which can be simple permanent bar magnets or, more preferably in this embodiment, a series of electromagnets. Such electromagnets when operated in conjunction with a second set of peripheral electromagnets 250 can cause the blade 14B to advance across the guiding edge of the reference member by electromotive force with virtually no physical contact between the blade and any motorized driving elements. The mechanism illustrated in FIGS. 19–21 is essentially a magnetic propulsion system similar to that used in modern "mag-lev" railway transportation.

With reference back to FIG. 1, the present invention is ideally suited for the removal of thin layers of corneal tissue. When reference member 12 is placed in contact with the corneal surface, it can be used to remove the epithelium or a precise layer of corneal tissue of predefined thickness. The thickness of the removed lamella is determined by the shape of the interior distal surface of the reference member and, in some instances, the tension of the cutter. The distal end is formed so as to have a cavity which captures a predefined volume (and thickness) of tissue 4. When the cutting element 14 has completed its path from point A to point B as shown in FIG. 1, a lamella of defined volume and thickness is captured within the cavity of the reference member.

Figure 22:
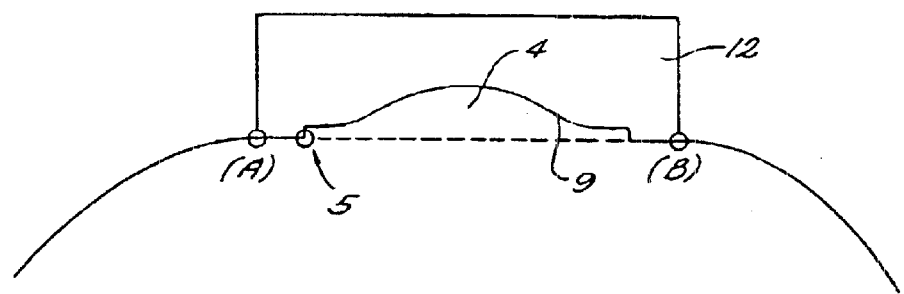
FIG. 22 is a schematic illustration of another embodiment of the ocular reference member.

In FIG. 22 another preferred aspect of the invention is schematically illustrated. The disclosed technique solves a fundamental problem in the use of conventional keratomes, that being, the difficulty in initiating a cut. As illustrated in FIG. 22, the desired action of the cutter in accordance with the present invention is to traverse the cornea from point (A) to point (B) along the guiding edge 8, thereby excising or hingedly displacing the volume of tissue 4 within the cavity of the reference member 12. The most common problem in keratome operation of this type is the initiation of the cut because the knife or other cutting instrument must attack the corneal surface along a line that is nearly tangential. Often this initial incision of the blade is less than perfect and results in a tear or other non-optimal resection.

The present invention solves this problem by creating a cavity that includes a small step 5 at the point of incision. The overall curvature 9 of the reference member 12 remains uniform and approximates the predetermined ideal shape for the removal of a cap or lentical. However, the creation of the step will result in a "rim-like" surface deformity at the periphery of the eye. In most instances this deformity will be sufficiently distant from the optical zone to avoid any interference with vision and, as explained in more detail below, when the excision is intended to simply form a hinged flap, the step-like deformity will be alleviated when the cap layer is replaced on the corneal surface.

Figure 23:
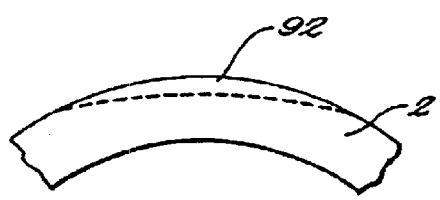
FIG. 23 illustrates a general class of corneal surgery procedures involving the removal of a thin layer of corneal tissue which can be carried out with the apparatus of the present invention.

In FIG. 23, the operation of the instrument is again illustrated schematically in a general manner. By appropriate design of the reference member, the tissue surface 2, as shown in FIG. 23 can be modified by removal of the lamella 92. To remove a lamella, the tissue need only be pliable enough to conform itself to the shape of the cavity 9 at the distal end of the reference member 12 (as shown in FIG. 1). For a particular cavity design, the shape and volume of the removed lamella will be same regardless of the tissue type so long as the tissue is pliable and incompressible at the level of pressure applied. Because the referencing of the tissue by the reference member takes place on a very local basis, precision can be achieved despite alterations in external conditions. Thus, the accuracy of the lamella resection is largely immunized from disruption by breathing, heartbeat, involuntary patient twitches, and/or the manual movements of the clinician during the procedure.

The removal of a tissue lamella may be desirable for therapeutic purposes (e.g. removal of an abnormal growth or ulcerous condition) and, especially, when the tissue 2 is corneal tissue, as a step in refractive correction. In the schematic illustration of FIG. 23, the removal of lamella 92 imparts a flattened curvature to the cornea and can be used to correct myopia. It should be clear that the distal end of the reference member 12 can be shaped in alternative forms to correct hyperopia, astigmatism and any combination of these conditions, as well. In addition, the cavity can take the form of a flat pan recess to remove corneal lamella of a standard thickness (e.g. "donor buttons") for transplantation purposes or for freeze-lathing keratomileusis. Moreover, a flat pan recessed cavity can also be useful in obtaining tissue biopsy samples of standardized depth and volume for cancer detection and other diagnostic purposes.

Figure 24A:
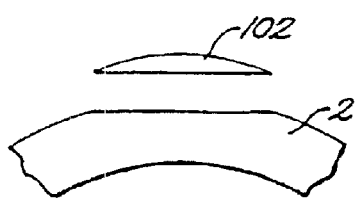
FIGS. 24A–24C illustrate a second class of corneal surgery procedures which can be carried out with the present invention.
Figure 24B:
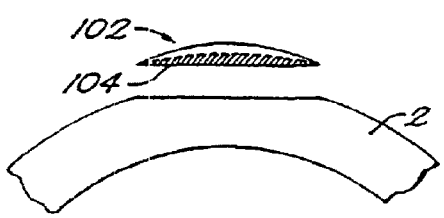
Figure 24C:
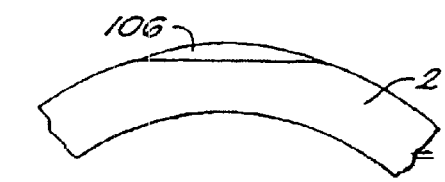

The apparatus of the present invention can also be used as a conventional keratome to simply resect a lamella 102 from the cornea 2 as shown in FIG. 24A. The resected lamella can then be shaped by conventional keratomileusis techniques (e.g., freezing and lathing) to remove a portion 104 of the lamella 102 as illustrated in FIG. 24B. This modified lamella 106 can then be replanted upon the corneal surface, as known in the art, as illustrated in FIG. 24C.

Figure 25A:
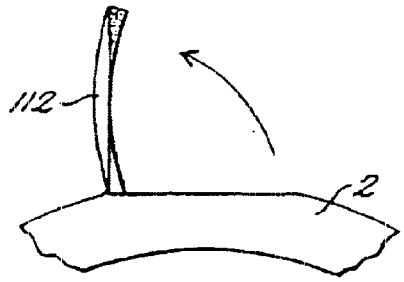
In FIGS. 25A–25C yet another corneal surgery procedure is shown.
Figure 25B:
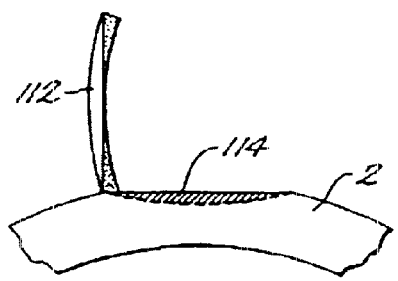
Figure 25C:
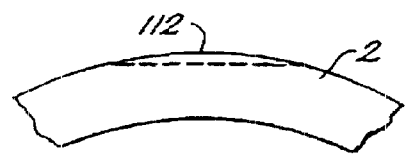

In addition, the instruments of the present invention can be used to facilitate mechanical sculpting and LASIK procedures by either removing (or hingedly displacing) a lamella 112 from the corneal surface 2 as illustrated in FIG. 25A. In such mechanical sculpting and LASIK procedures, the exposed stromal bed can then be reshaped as desired to provide refractive correction as illustrated schematically in FIG. 25B. As a final step in these procedures, the lamella 112 is replaced upon the cornea and reattached by known surgical techniques, as shown in FIG. 25C. To facilitate realignment, the corneal periphery and/or the lamella can be marked by various techniques known in the art prior to cutting). The invention can also be used to simply remove the epithelium, e.g., with its basement membrane intact, in other applications.

Figure 26:
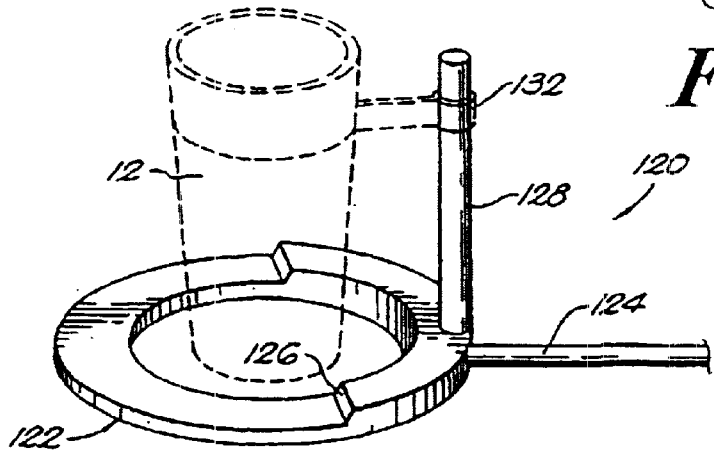
FIG. 26 illustrates a further aspect of the invention including a guide ring which can be used to join and/or align the apparatus of the present invention with a target biological tissue surface.

In FIG. 26, a guide ring 120 is shown which can be used to join and/or align a reference member 12 (shown in phantom) and a tissue surface. Guide ring 120 can be used to secure the reference member in place. Various techniques can be employed to affix the guide ring to the corneal surface. For example, a vacuum line 124 can be connected to the ring 120 such that a plurality of orifices in the bottom surface 122 of the ring is used to secure the ring to the cornea by suction. Alternatively, the guide ring can include an adhesive coating or a plurality of pins which penetrate into the stroma during use and anchor the device in place. The reference member 12 and suction ring 120 preferably are joined together, e.g., by post 128 and mounting flange 132, such that the reference member is fixed in a desired position on the cornea.

Guide ring 120 of FIG. 26 also illustrates one mechanism for controlling the lamellar resection to create a flap of tissue (as opposed to completely severing the tissue segment) for use in mechanical sculpting and LASIK procedures. Stop surface 126 of ring 120 is designed such that the cutting element cannot travel the entire distance along the path of the guiding edge of the reference member. As the cutting assembly (not shown) travels from its initial position until contacting the blocking surface 126 the tissue segment is sliced away from the corneal surface. However, when the cutting assembly reaches the block 126, the cutting action can be terminated, automatically or manually. (Partial resections can also be achieved by activation of the guillotine mechanism 38, as shown in FIG. 4, before the cutter has completed its traverse of the surface).

Figure 27:
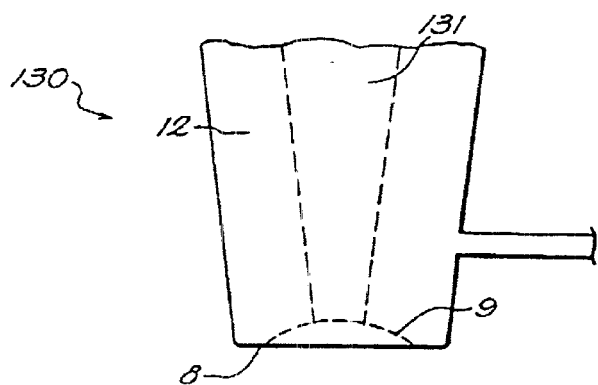
FIGS. 27 and 28A–B illustrate further alternative structures for joining the reference member to a tissue target site.
Figure 28A:
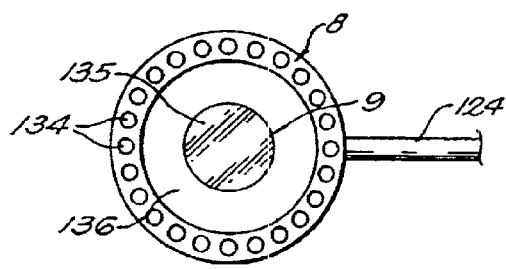
Figure 28B:
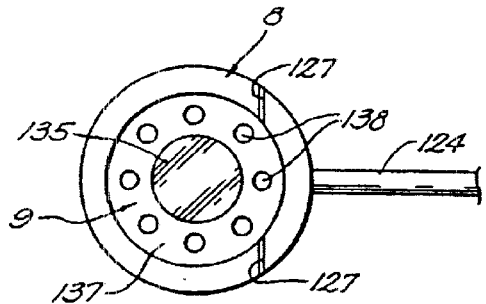

In FIGS. 27 and 28A–B, alternative support mechanisms for locally securing the reference member to the target tissue region are shown. Thus, as shown in FIG. 27, an assembly 130 can include a reference member 12 and a vacuum source 124. The reference member included a guiding edge 8 and a cavity 9, as well as an optional viewing tube 131. FIG. 28A illustrates an embodiment in which the vacuum source attaches the reference member 12 to the tissue via on or more ports 134 on the guiding edge. In addition, a portion 136 of the internal cavity surface can be textured or coated with an adhesive material. If viewing is desired, a portion 135 of the cavity surface can remain non-textured (and/or non-coated) and transparent to facilitate viewing. In another alternative shown in FIG. 28B, the reference member can be secured to the tissue by one or more suction ports 138 incorporated into the cavity 9 as well as optional frictional or adhesive regions 137 between such suction ports. In the embodiment of FIG. 28B, the guiding edge 8 is free of any securing structures to ensure smooth passage of the cutter and a central transparent region of the cavity is again preserved to allow viewing, if desired. As shown in FIG. 28B, the edge can also include a stop mechanism 127 to facilitate partial resections (e.g., for mechanical or LASIK stromal sculpting procedures). The stop mechanism 127 can be a groove recessed into the guiding edge 8 which captures the cutter (or triggers a guillotine mechanism that severs the cutter before complete resection occurs).

As noted above, reference member 12 can incorporate a variety of shaped cavities to facilitate removal of lamella of any desired shape and thickness. If the guiding edge of the reference member is planar, the shape of the removed lamella is simply determined by the cavity design. For astigmatic corrections, the cavity can take an ellipsoid rather than spherical shape.

Figure 29:
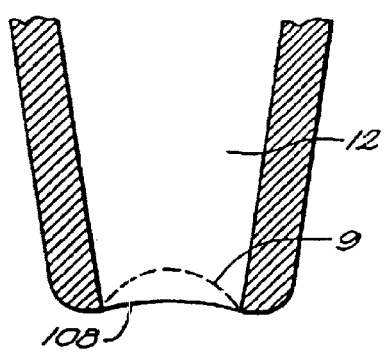
In FIG. 29 a further aspect of the invention is schematically illustrated wherein the guiding surface of the reference member is non-planar.

However, shaping can also be accomplished by variation of the form of the guiding edge of the reference member. As illustrated in FIG. 29, the reference member 12 can have a non-linear (non-planar) guiding edge 118. This permits additional design flexibility in the construction of reference member shapes to address various astigmatic corrections.

Moreover, the unique property of the non-planar guiding edges allows tremendous flexibility while maintaining precise control over the shape of the resected lamella. Unlike known keratomes which rely upon an inherently planar cutting action, the present invention permits non-planar shaping operations.

Figure 30:
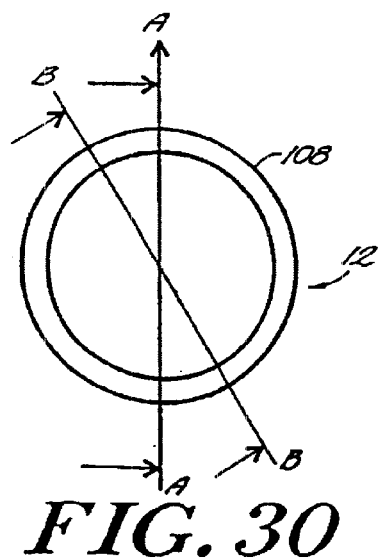
FIG. 30 illustrates a further class of procedures particularly useful with the apparatus of FIG. 29 in which the orientation of the cutting element vis-à-vis the reference member is varied.

In addition, because the present invention makes non-planar cutting operations feasible, the number of different reference member cavity shapes necessary to treat the various astigmatic problems exhibited by a population can be reduced. With reference to FIG. 30, the utility of a non-planar guiding edge is illustrated further. As shown in the figure, reference member 12 and non-planar guiding edge 18 define a cutting path as the cutting element is drawn across the surface of the distal surface of the system (as illustrated by the path A—A). Such a cut will create a lamella of a predefined shape.

If the azimuthal angle of attack is modified, as shown schematically in FIG. 30 by line B—B, it should be clear that an entirely different shape will be resected. Thus, by either rotating the cutting mechanism vis-à-vis the reference member (or vice-versa) to a desired orientation prior to activation, a whole set of different shapes can be removed from the tissue surface using a single reference member design. With reference again to FIG. 2, the azimuthal orientation of the cutter assembly can.be adjusted by selecting a particular mounting location for pivot bearing assembly 22 along the circular ring 21. Alternatively, with reference to FIG. 6, the azimuthal orientation can be adjusted by rotation of sleeve 17. Other orientation mechanisms will be apparent to those skilled in the art.

Figure 31:
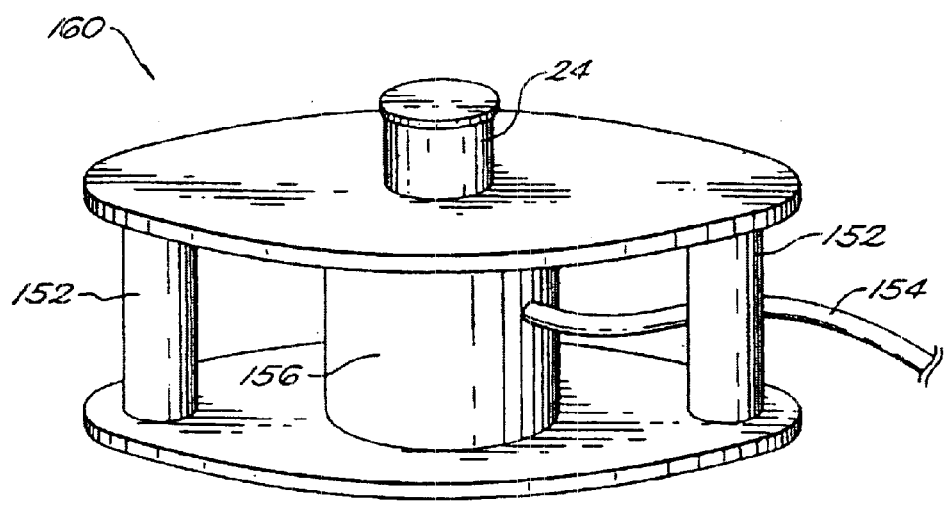
FIG. 31 illustrates a casement for housing an apparatus according to the invention.

In FIG. 31, a housing 160 is shown for the systems of the present invention suitable for hand-held operations. The housing 160 includes hand grips 152 so that the surgeon can hold the instrument between his or her fingers. (Preferably, the surgeon also uses the base of his or her hands and/or the smaller fingers to hold the patient's head during the corneal resection.) As further shown in FIG. 31, the proximal end of the viewing tube 24 projects from the top of the housing 160 and the reference member itself is disposed upon the eye at the bottom of the housing (not shown). The instrument can also include a conduit 154 to provide of electrical power and/or suction to facilitate attachment on the eye. The housing 160 further includes a protrusion that encases the cutter assembly and permits its movement into and out of engagement with the reference member.

Figure 32:
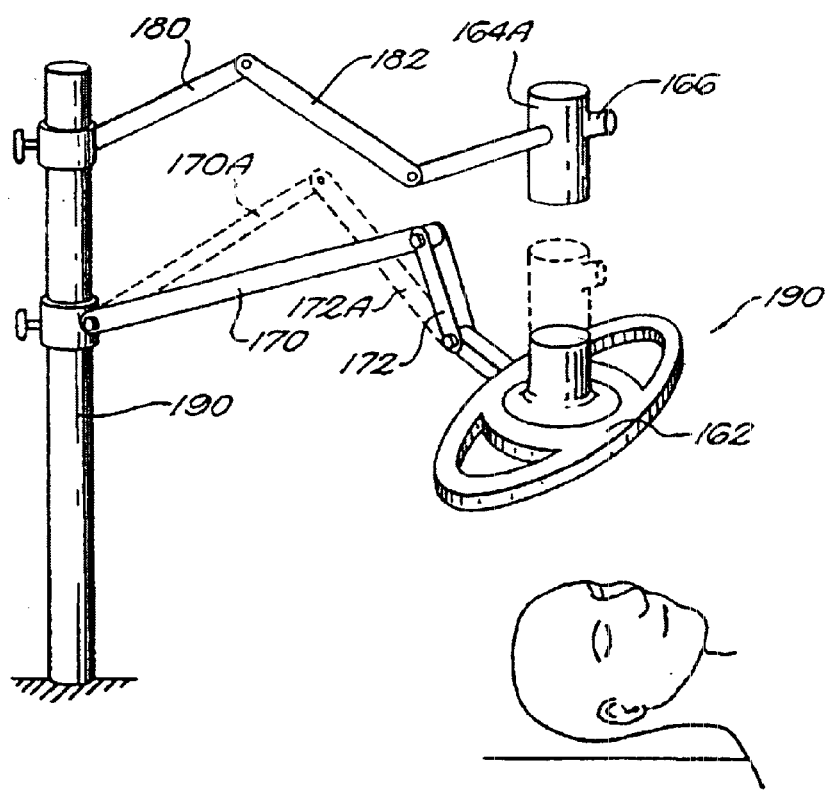
FIG. 32 illustrates an overall system for corneal refractive surgery employing the present invention.

In FIG. 32, an overall system for eye surgery 190 is shown including a housing 162 (similar to that described above in FIG. 31) mounted for mechanical engagement upon the cornea. Pivot arms 170 and 172 as well as swivel joint 174 allow movement of the housing 162 in the x, y and z directions while preventing angular tilting movements that might interfere with precise alignment. Movement of the housing 162 up and down can be accomplished by the adjustment of the pivot arms 170 and 172 (as shown schematically in phantom by alternative positions 170A and 172A).

Also shown in FIG. 17 is a surgical microscope 164 which can be joined to housing 162 (as shown in phantom) or carried by an independent housing 164A similarly mounted via pivot arms 180 and 182 for rectilinear movement. In use, the patient's head can be immobilized or a fixation light 166 can be employed to create a visual sight line when the patient fixes his or her gaze on the light to automatically align the system with the optical (or visual) axis of the eye.

What is claimed is:

1. In a surgical apparatus comprising a cutter for slicing a lamellar segment from a biological tissue, the improvement comprising: a reference member for securing a selected portion of tissue, the reference member adapted to engage the tissue and a peripheral, guiding edge integral with, or coupled to, the reference member for guiding said cutter, said cutter further comprising a driver such that the cutter can be brought into physical contact with the guiding edge of the reference member and drawn through the biological tissue to effect removal of a lamellar segment of the tissue.

2. The apparatus of claim 1 wherein the cutter comprises a flexible cutting element.

3. The apparatus of claim 2 wherein the cutting element comprises a wire.

4. The apparatus of claim 2 wherein the cutting element comprises a band.

5. The apparatus of claim 1 wherein the cutter comprises a blade.

6. The apparatus of claim 1 wherein the cutter further comprises a reel mechanism for reeling the cutting element in at least one traverse direction as it is drawn through the tissue.

7. The apparatus of claim 1 wherein the cutter further comprises a swinging pendulum assembly for imparting a sweeping motion to the cutting element in order to draw it through the tissue.

8. The apparatus of claim 1 wherein the cutter further comprises a linear motive actuator in order to draw the cutter through the tissue.

9. The apparatus of claim 1 wherein the cutter further comprises a magnetic motive actuator in order to draw the cutter through the tissue.

10. The apparatus of claim 1 wherein the reference member has a non-planar guiding edge which defines a non-planar cut.

11. The apparatus of claim 1 wherein the apparatus further comprises at least one magnetic element for urging the cutter into contact with a guiding edge of the reference member.

12. The apparatus of claim 1 wherein the apparatus further comprises at least one orientation marker for orienting the reference member vis-à-vis the path of the cutter.

13. The apparatus of claim 1 wherein the reference member is at least partially transparent to facilitate viewing of the tissue during the cutting.

14. The apparatus of claim 1 wherein the reference member further comprises means to secure the tissue surface to the reference member, for example, by either suction, a frictionally adherent surface or an adhesive coating to physically bind the tissue surface to the reference member.

15. The apparatus of claim 1 wherein the apparatus further comprises an optical viewing assembly adapted for optical alignment, or direct coupling with a video camera.

16. The apparatus of claim 1 wherein the tissue engaging surface of the reference member is shaped to create a peripheral step at the point of initial cutter incision so as to facilitate entry of the cutter into the tissue.

17. The apparatus of claim 1 wherein the apparatus is further adapted to secure a cornea of an eye to the reference member.

18. The apparatus of claim 17 wherein the apparatus further comprises a vacuum source to secure the cornea to the reference member by suction.

19. The apparatus of claim 17 wherein the apparatus further comprises a vacuum source and the reference member has a porous tissue engaging surface, which when coupled to the vacuum source effects tissue adhesion.

20. The apparatus of claim 17 wherein the reference member further comprises a frictionally adherent surface to physically bind the cornea to the reference member.

21. The apparatus of claim 17 wherein the reference member further comprises an adhesive coating to physically bind the cornea to the reference member.

22. The apparatus of claim 17 wherein the reference member further comprises a mechanical means for physically binding the cornea to the reference member.

23. The apparatus of claim 17 wherein the apparatus further comprises an optical viewing assembly adapted for optical alignment, or direct coupling with a surgical microscope.

24. The apparatus of claim 17 wherein the apparatus further comprises a stop mechanism to ensure that the lenticule is only partially severed.

25. The apparatus of claim 17 wherein the apparatus further comprises a support body comprising a receptacle for receiving the reference member and when coupled to the reference member forms, at least in part, guiding edge for guiding a cutter such that the cutter can be brought into contact with the guiding edge of the reference member and drawn through the tissue to effect removal of a lamellar segment of the tissue.

26. The apparatus of claim 1 wherein the cutter further comprises an oscillator for imparting an oscillating motion to the flexible cutting element as it is drawn through the tissue.

27. The apparatus of claim 1 wherein the guiding edge is an integral with the reference member.

28. The apparatus of claim 1 wherein the guiding edge is coupled to the reference member.

29. An reference member for use in a surgical apparatus for removing a lamellar segment from biological tissue with a cutter, the reference member comprising a reference body surface adapted to engage a tissue surface and having a peripheral, guiding edge for guiding a cutter such that the cutter can be brought into contact with the guiding edge of the reference member and drawn through the tissue to effect removal of a lamellar segment of the tissue.

30. The apparatus of claim 29 wherein the reference member has a non-planar guiding edge which defines a non-planar cut.

31. The apparatus of claim 29 wherein the apparatus further comprises an orientation marker for orienting the reference member vis-à-vis the path of the cutter.

32. The apparatus of claim 29 wherein the reference member is at least partially transparent to facilitate viewing of the tissue during the cutting.

33. The apparatus of claim 29 wherein the reference member further comprises means to secure the tissue surface to the reference member, for example, by either suction, a frictionally adherent surface or an adhesive coating to physically bind the tissue surface to the reference member.

34. The apparatus of claim 29 wherein the tissue engaging surface of the reference member is shaped to create a peripheral step at the point of initial cutter incision so as to facilitate entry of the cutter into the tissue.

35. The apparatus of claim 29 wherein the tissue engaging surface of the reference member is porous.

* * * * *